US008177840B2

(12) United States Patent
Linares

(10) Patent No.: US 8,177,840 B2
(45) Date of Patent: May 15, 2012

(54) ARTIFICIAL LIGAMENTS FOR JOINT APPLICATIONS AND INCLUDING RESISTIVE RETAINING AND END DEFORMING CHARACTERISTICS

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 79 days.

(21) Appl. No.: 12/708,094

(22) Filed: Feb. 18, 2010

(65) Prior Publication Data

US 2010/0145450 A1  Jun. 10, 2010

Related U.S. Application Data

(62) Division of application No. 12/212,141, filed on Sep. 17, 2008, now Pat. No. 7,887,586.

(60) Provisional application No. 60/972,903, filed on Sep. 17, 2007, provisional application No. 61/031,187, filed on Feb. 25, 2008.

(51) Int. Cl.
*A61F 2/08* (2006.01)

(52) U.S. Cl. ............... 623/13.14; 623/13.11; 623/13.12; 623/13.13; 623/13.15

(58) Field of Classification Search .... 623/13.11–13.18, 623/17.11–17.19, 20.11, 20.26–20.33; 606/186, 606/232, 286; 604/399
See application file for complete search history.

(56) References Cited

U.S. PATENT DOCUMENTS

| | | |
|---|---|---|
| 2,667,644 A | 2/1954 | Johnson |
| 3,973,277 A | 8/1976 | Semple et al. |
| 4,483,023 A | 11/1984 | Hoffman, Jr. et al. |
| 4,501,031 A | 2/1985 | McDaniel et al. |
| 4,665,951 A | 5/1987 | Ellis et al. |
| 4,744,793 A | 5/1988 | Parr et al. |
| 4,778,473 A | 10/1988 | Matthews et al. |
| 4,792,336 A | 12/1988 | Hlavacek et al. |
| 4,828,562 A | 5/1989 | Kenna |
| 4,851,005 A | 7/1989 | Hunt et al. |
| 4,883,486 A | 11/1989 | Kapadia et al. |

(Continued)

FOREIGN PATENT DOCUMENTS

WO 2009039164 A1 3/2009

OTHER PUBLICATIONS

Tan et al., "Developments of an Antimicrobial Microporous Polyurethane Membrane", Journal of Membrane Science, 289. 199-209 (2007).

*Primary Examiner* — David Isabella
*Assistant Examiner* — Yashita Sharma
(74) *Attorney, Agent, or Firm* — Gifford, Krass, Sprinkle, Anderson & Citkowski, P.C.

(57) ABSTRACT

A ligament incorporated into a prosthetic joint exhibiting a plasticized, elongated and deformable material. A fibrous material is internally disposed within the deformable material, the fibrous material terminating in first and second enlarged bead portions arranged in proximity to enlarged pocket defined ends associated with the deformable materials. First and second bones define a joint region therebetween, the deformable end pockets and bead portions being inserted through associated holes defined in joint proximate locations associated with the bones, so that actuation of a projection location of the fibrous material causes the bead portions to outwardly deflect the end pockets, resulting in the ligaments being anchored in place between the bones.

4 Claims, 11 Drawing Sheets

U.S. PATENT DOCUMENTS

| | | | |
|---|---|---|---|
| 5,004,474 A | 4/1991 | Fronk et al. | |
| 5,078,745 A | 1/1992 | Rhenter et al. | |
| 5,171,325 A | 12/1992 | Aulie | |
| 5,263,984 A | 11/1993 | Li et al. | |
| 5,282,867 A | 2/1994 | Mikhail | |
| 5,376,119 A | 12/1994 | Zimmermann et al. | |
| 5,389,107 A | 2/1995 | Nassar et al. | |
| 5,417,693 A | 5/1995 | Sowden et al. | |
| 5,486,197 A | 1/1996 | Le et al. | |
| 5,554,194 A | 9/1996 | Sanders | |
| 5,571,191 A | 11/1996 | Fitz | |
| 5,575,819 A | 11/1996 | Amis et al. | |
| 5,676,702 A | 10/1997 | Ratron et al. | |
| 5,707,395 A * | 1/1998 | Li | 606/232 |
| 5,728,175 A | 3/1998 | Rincoe | |
| 5,800,566 A | 9/1998 | Gramnas et al. | |
| 5,879,404 A | 3/1999 | Bateman et al. | |
| 5,921,358 A | 7/1999 | Gramnas et al. | |
| 6,001,106 A | 12/1999 | Ryan et al. | |
| 6,010,535 A | 1/2000 | Shah | |
| 6,190,411 B1 | 2/2001 | Lo et al. | |
| 6,245,109 B1 | 6/2001 | Mendes et al. | |
| 6,325,804 B1 | 12/2001 | Wenstrom, Jr. et al. | |
| 6,383,223 B1 | 5/2002 | Baehler et al. | |
| 6,582,715 B1 * | 6/2003 | Barry et al. | 424/422 |
| 6,626,942 B1 | 9/2003 | Edberg et al. | |
| 6,645,251 B2 | 11/2003 | Salehi et al. | |
| 6,840,962 B1 | 1/2005 | Vacanti et al. | |
| 6,939,379 B2 | 9/2005 | Sklar | |
| 7,044,983 B1 | 5/2006 | Cheng et al. | |
| 7,056,340 B2 | 6/2006 | McKernan et al. | |
| 7,066,958 B2 | 6/2006 | Ferree | |
| 7,087,091 B1 | 8/2006 | Chen et al. | |
| 7,101,398 B2 | 9/2006 | Dooris et al. | |
| 7,153,327 B1 | 12/2006 | Metzger | |
| 7,175,666 B2 | 2/2007 | Yao | |
| 7,329,281 B2 | 2/2008 | Hays et al. | |
| 7,331,995 B2 | 2/2008 | Eisermann et al. | |
| 7,708,781 B2 | 5/2010 | Scheker | |
| 2001/0051831 A1 | 12/2001 | Subba Rao et al. | |
| 2002/0013627 A1 | 1/2002 | Geistlich et al. | |
| 2004/0024460 A1 | 2/2004 | Ferree | |
| 2005/0187620 A1 | 8/2005 | Pai et al. | |
| 2005/0192674 A1 | 9/2005 | Ferree | |
| 2006/0074423 A1 | 4/2006 | Alleyne et al. | |
| 2006/0149370 A1 | 7/2006 | Schmieding et al. | |
| 2007/0005137 A1 | 1/2007 | Kwak | |
| 2009/0039164 A1 | 2/2009 | Herwig et al. | |
| 2009/0292364 A1 | 11/2009 | Linares | |

* cited by examiner

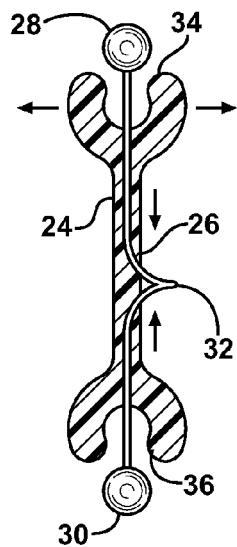 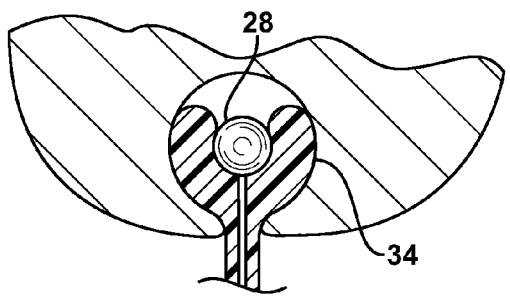 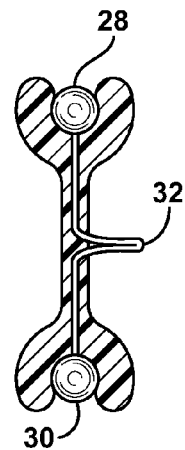
FIG. 3  FIG. 3A  FIG. 3B
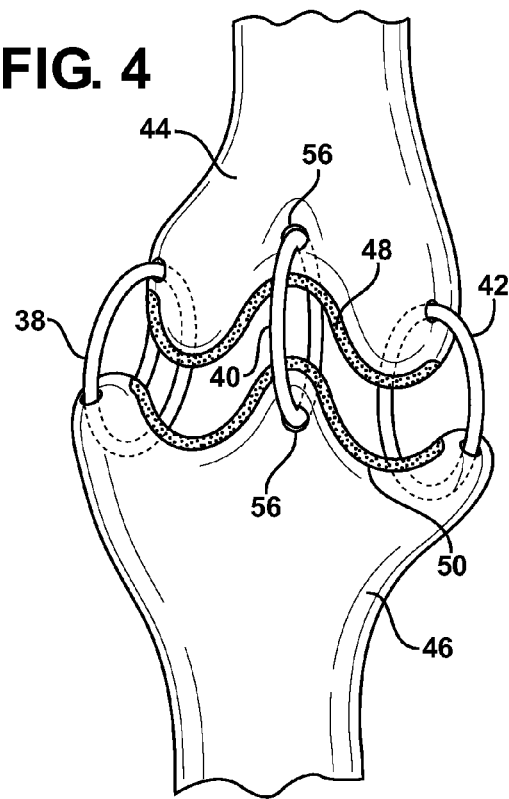 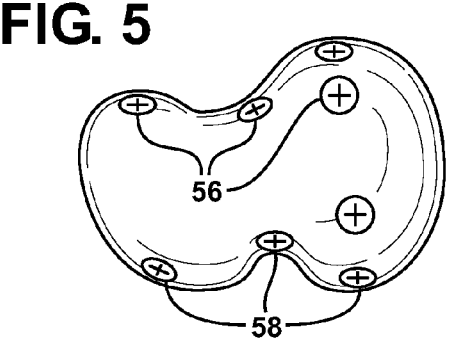
FIG. 4  FIG. 5

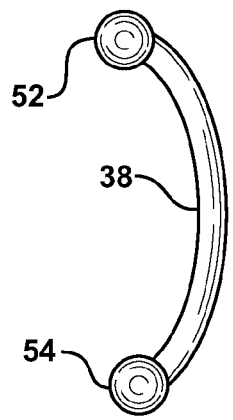 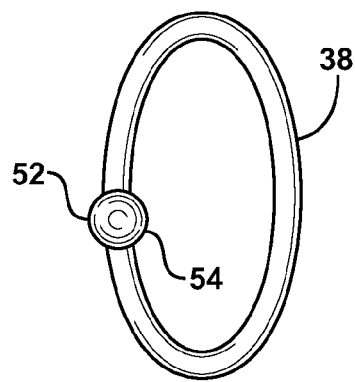 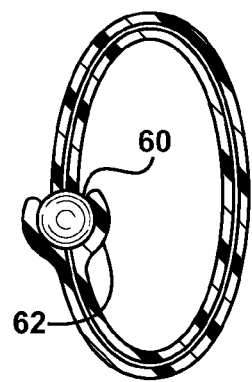
FIG. 6   FIG. 6A   FIG. 6B
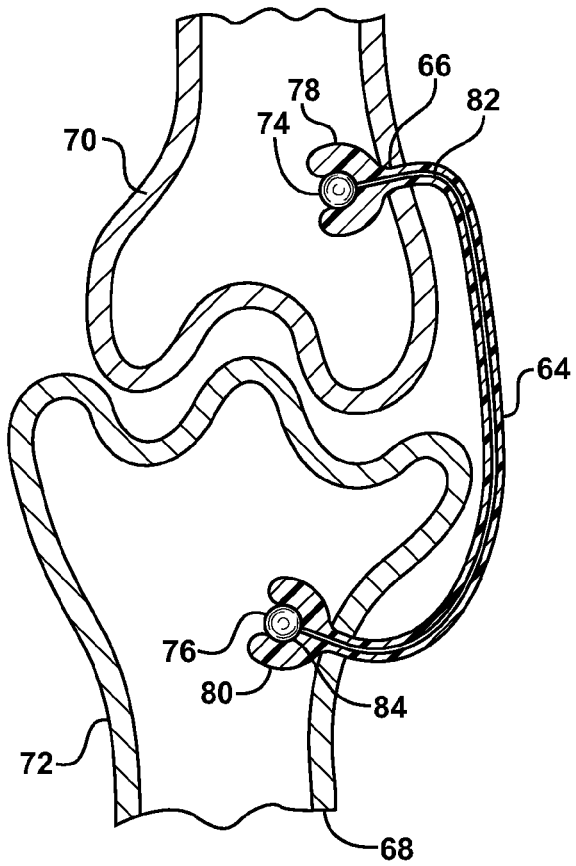
FIG. 7

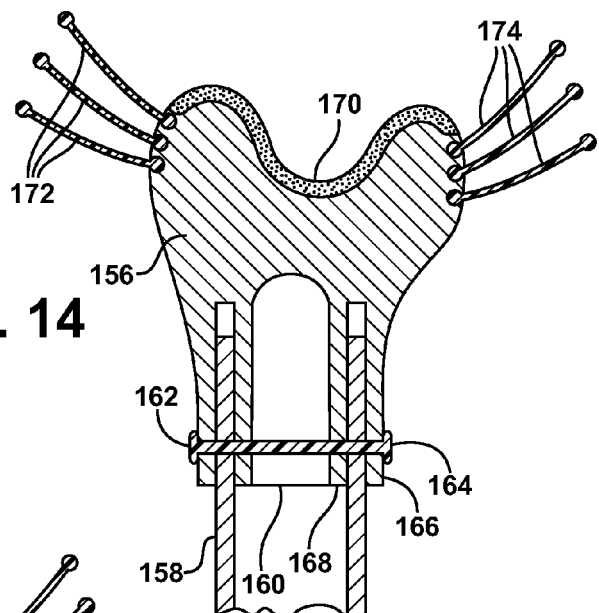
FIG. 14
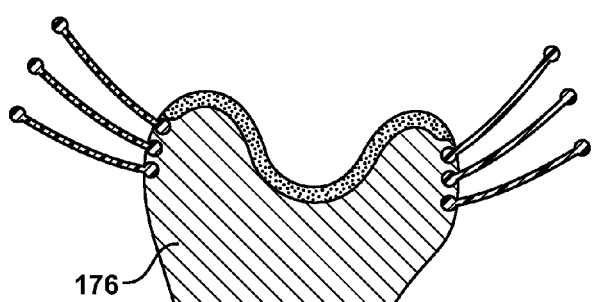
FIG. 15
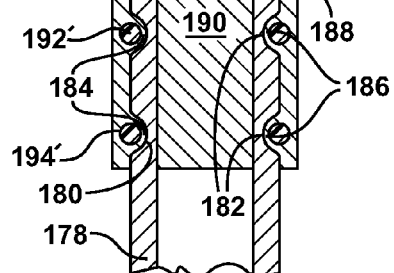
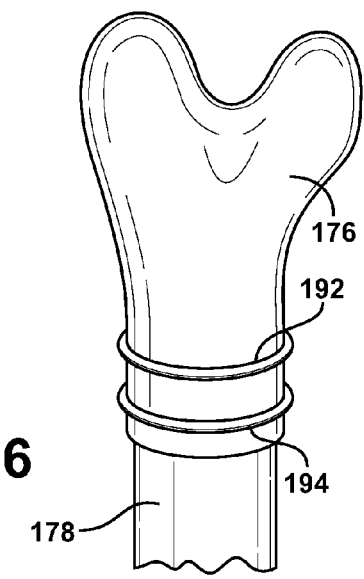
FIG. 16

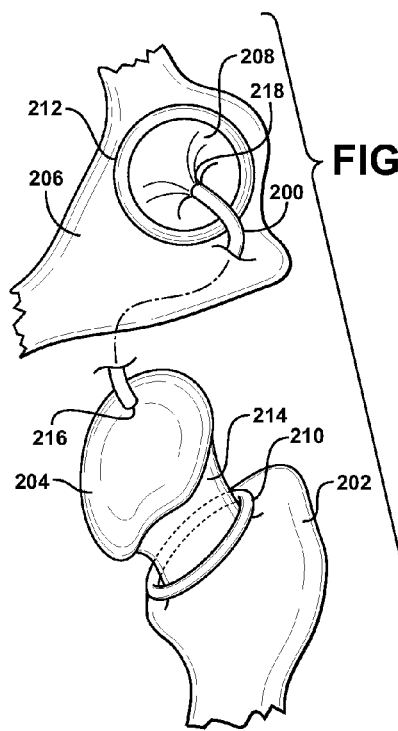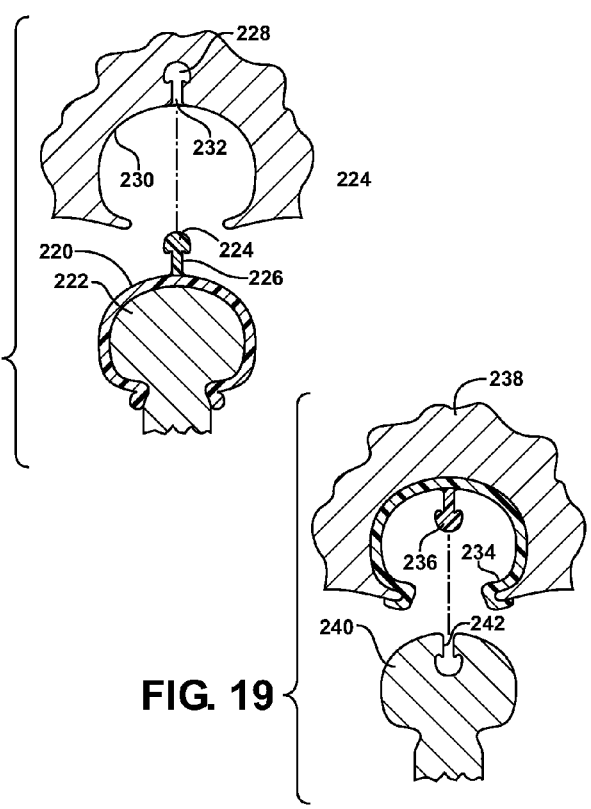
FIG. 17
FIG. 18
FIG. 19

ARTIFICIAL LIGAMENTS FOR JOINT APPLICATIONS AND INCLUDING RESISTIVE RETAINING AND END DEFORMING CHARACTERISTICS

CROSS-REFERENCE TO RELATED APPLICATIONS

This Application is a divisional of U.S. patent application Ser. No. 12/212,141 filed Sep. 17, 2008, which claims the benefit of Provisional Patent Application Nos. 60/972,903, filed on Sep. 17, 2007, and Provisional Application Ser. No. 61/031,187, filed on Feb. 25, 2008.

FIELD OF THE INVENTION

The present invention is concerned with artificial implants for use with both natural and artificial human bones. In particular, the present inventions discloses a number of ligament supports, such as are capable of substituting for human ligaments in an artificial implant. The artificially constructed ligament provides for non deforming stretching and contracting, such as is associated with natural ligaments and tendons, this assisting in maintaining the integrity of an joint established between first and second opposing bone ends of an artificial implant.

In a further application, the present inventions disclose an improved ligament support configuration, such as are capable of substituting for human ligaments in an artificial implant. The artificially constructed ligament includes a cup and cavity sealing arrangement, between a first bone defined ball projection and an associated ball socket. An interiorly configured ligament, extending between an interior location of the socket and an end surface of the associated projection, provides a measure of deformable and non-tear stretching and contracting, and such as is associated with natural ligaments and tendons, this assisting in maintaining the integrity of an joint established between first and second opposing bone ends of an artificial implant. The configuration is particularly suited for use in replacement or rehabilitative knee joint assemblies, in one variation for the particular benefit of adolescents, and which provides a unique and dynamic joint design.

BACKGROUND OF THE INVENTION

The prior art is documented with various types of prosthetic ligament assemblies, these typically being provided with an artificial joint, the purpose for which being to replace an existing joint and ligaments which has become worn through extended wear or irreplaceably damaged through disease or injury. One objective of such artificial joint/ligament implants, whether adapted for use with an existing bone remaining in the patient or as a component of one or more skeletal implants which includes a built-in joint, is in providing a desired amount of cushioning and restraining support when positioned in-situ. Examples of existing natural/synthetic engineered ligament and tendon articles, methods and assemblies include, among others, those set forth in Vacanti U.S. Pat. No. 6,840,962, Parr U.S. Pat. No. 4,744,792, Li U.S. Pat. No. 5,263,984, Dooris U.S. Pat. No. 7,101,398, Lo U.S. Pat. No. 6,190,411, Hays U.S. Pat. No. 7,329,281, Zimmermann U.S. Pat. No. 5,376,119, Sklar U.S. Pat. No. 6,939,379, Fronk U.S. Pat. No. 5,004,474, Edberg U.S. Pat. No. 6,626,942, Hlavacek U.S. Pat. No. 4,792,336, Kapadia U.S. Pat. No. 4,883,486, Hoffman U.S. Pat. No. 4,483,023, Semple U.S. Pat. No. 3,973,277, McKernan U.S. Pat. No. 7,056,340, Ryan U.S. Pat. No. 6,001,106 and, finally, Kenna U.S. Pat. No. 4,828,562.

SUMMARY OF THE INVENTION

In a first application, the present inventions disclose a ligament for incorporating into an artificial joint associated with an implant. Each ligament includes a plasticized, elongated and deformable material. A fibrous material is internally disposed within the outer deformable material, with the fibrous material terminating in first and second enlarged bead portions arranged in proximity to enlarged pocket defined ends associated with the deformable materials.

First and second bones define a joint region therebetween, with deformable end pockets and bead portions being inserted through associated holes defined in joint proximate locations associated with the bones. Actuation of a projection location of the fibrous material causes the bead portions to outwardly deflect their associated end pockets, resulting in the ligaments being anchored in place between the bones.

In a preferred application, the ligaments each include an outer urethane body, with the fibrous material including at least one of a graphite, a nylon, a polyester, and a cellulosic fiber strand material. The ligaments can also exhibiting any of a linear, an arcuate and a circular/ring shape.

In another sub-application, an alternately configured and press fit ligament structure possesses an elongated body with laterally projecting and barbed side sections, the sections being "press fit" into engagement with side disposed locations of a selected bone or pair of bones located in closely proximate fashion. The press fit ligament structure possesses an elongated body with laterally projecting and barbed side sections which are "press fit" into engagement with side disposed locations of a selected bone or pair of bones located in closely proximate fashion.

In a further sub-application, a plurality of plasticized plugs coaxially secure an end-defined implant section over an elongate, open ended and interiorly hollowed artificial bone. In another, an end section implant is engaged over an artificial bone, and exhibits undercut sections established in the outer annular bone, these inter-fitting with a corresponding and annular interior configuration associated with a depending skirt portion of the annular end implant section. Plastic bands can also be provided for securing the end-fitted implant section over the hollow bone.

In a further embodiment, the ligament is incorporated into the artificial joint associated with the implant and includes first and second bones defining a joint region therebetween. A lubricating plastic is defined upon an exposed face of at least one, and typically both, of the bones. One or more "dynamic" ligament portions extend from at least the lubricated plastic and secure to an exposed and opposing end face of the other of the bones.

The first bone typically exhibits a bulbous and ball shaped projecting portion, with the second bone exhibiting an interiorly recessed and three dimensional socket receiving portion for receiving the ball shaped portion in seating fashion. The ligaments further each exhibit bulbous end projection portions, these extending from an interconnecting neck portion and secured to a surface of the lubricating plastic. The bulbous projections secure into an interiorly formed recess defined in an opposing bone surface.

The lubricating plastic is secured to either of the bulbous projection or interiorly formed recess and further includes opposing and mating lubricating plastic surfaces provided as ring-shaped components secured to opposing and coating surfaces of each of the bones, such that the rings contact one another in a mating and relatively rotational permissive fashion and in order to promote effortless contact between the exposed and opposing end surfaces. The ligament portions can also include a pair of crosswise extending ligaments secured to opposing and joint defining surfaces associated with first and second artificial end plugs in turn mounted to the bones. In another application, a swivelable joint assembly is provided in which a rotating flexible ligament of substantial spool shape is arranged in a socket configuration between a lower male end defining bone and an undercut support secured to an upper socket defining bone.

BRIEF DESCRIPTION OF THE DRAWINGS

Reference will now be made to the attached drawings, when read in combination with the following detailed description, wherein like reference numerals refer to like parts throughout the several views, and in which:

FIG. 3 is a first illustration of a ligament sub-assembly, in a pre-tensioned/anchored condition once opposite ends of the ligament are located through mounting drill hole locations associated with first and second opposing and joint defining bones;

FIG. 3A is a succeeding illustration to FIG. 3 and showing a selected ligament end arranged within a bone drill hole;

FIG. 3B is a further succeeding illustration to that shown in FIG. 3 and referencing the fibrous/thread being progressively displaced in order to outwardly deform the outer urethane material associated with the ligament ends in biasing fashion against the arcuate inner walls of the bone drill hole;

FIG. 4 is an illustration of a ligament structure according to another embodiment and illustrating a plurality of ring-shaped ligaments;

FIG. 5 is an end view of a selected bone shown in FIG. 4;

FIG. 6 is an illustration of a semi-circular ligament, and such as can be employed in the variant of FIG. 4;

FIG. 6A illustrates a circular shaped ligament according to a further potential design;

FIG. 6B illustrates a modified version of the circular shaped ligament shown in FIG. 6A;

FIG. 7 is an illustration of an alternate mounting variant for securing an artificial ligament to first and second locations associated with a unique joint defining structure;

FIG. 14 is an illustration similar to that shown in FIG. 10 of a yet further anchor bolt design utilized in the securing of an end defined implant section over a bone, such as previously shown in FIG. 12;

FIG. 15 is an alternate embodiment for securing an end section over and artificial bone, and illustrating undercut sections established in the outer annular bone, these inter-fitting with a corresponding and annular interior configuration associated with a depending skirt portion of the annular end implant section; and FIG. 16 is a non-cutaway illustration of the embodiment of FIG. 15, and further showing the features of the plastic bands for securing the end-fitted implant section over the hollow bone.

FIG. 17 is an exploded view of a connective artificial ligaments incorporated into joint defining knee implant according to one embodiment of the present invention and including a first bone defined ball projection and an associated ball socket for establishing, in combination with a connective ligament, effortless contact between opposing bone end surfaces;

FIG. 18 is an exploded plan view illustrating a further variant of ligament assembly and in which a lubricated plastic layer surrounding the ball defined projection further includes an integrally formed, bulbous male end projecting ligament seating portion, this being resistively snap-fit received into an associated located recess in a female and additional bone defined socket cavity, for flexibly and dynamically retaining the first bone ball portion within the second bone socket of a selected artificial implant bone;

FIG. 19 is an exploded plan view of a further configuration of ligament assembly, similar to that shown in FIG. 2, and by which the arrangement of lubricating plastic layer and associated bulbous end ligament projection is switched to the female ball defined socket, the corresponding male ball projection incorporating an interior defined drill recess for resistively seating the ligament projection;

DETAILED DESCRIPTION OF THE PREFERRED EMBODIMENTS

Figure 1:
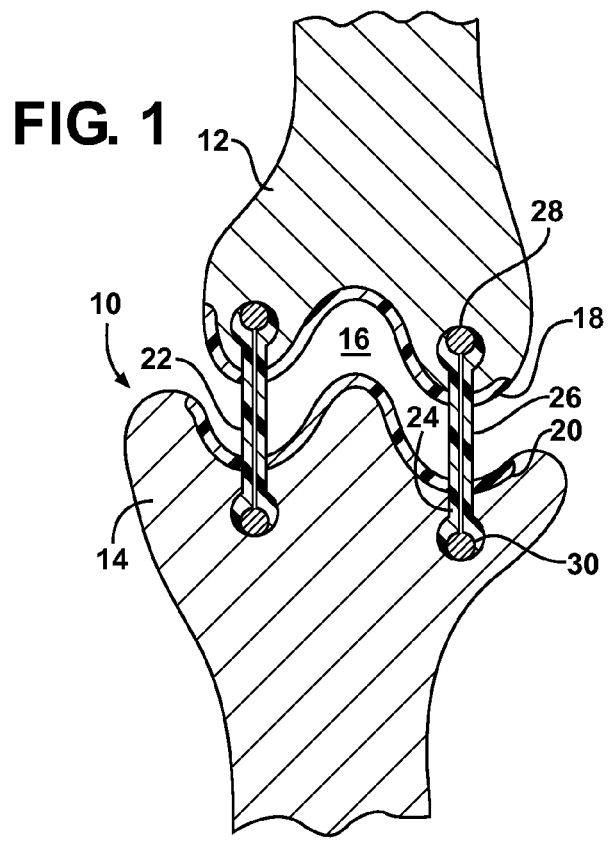
FIG. 1 is an illustration of artificial ligaments incorporated into joint defining knee implant according to one embodiment of the present invention and further including opposing and mating lubricating plastic surfaces for establishing effortless contact between opposing bone end surfaces.

Referring now to FIG. 1, a first embodiment is illustrated of an artificial ligament system incorporated into joint defining knee implant according to one embodiment of the present invention. The knee and ligament embodiment featured generally at 10 exhibits first 12 and second 14 bones, these typically corresponding to a patient's upper and lower leg bones and which further define particularly configured and opposing/seating locations which is defined as a joint region 16.

As further understood, the bones 12 and 14 are typically artificial prostheses, these including such as plastic, metal or other suitable material constructions which exhibit the necessary properties of durability and resilience. Opposing and mating lubricating plastic surfaces, see at 18 and 20, promote effortless contact between opposing bone end surfaces.

As will be further described with reference to FIGS. 3-3B, ligaments are shown at 22 and 24 (typically first and second pairs, totaling four are provided, with only a single pair evident from this illustration). The ligaments are each typically constructed of a fibrous based central core (see at 26 in FIG. 1 and also as referenced in the example of FIG. 3), over which is molded an expandable urethane or other suitable material, and such that the ligament exhibits the concurrent properties of significant durability, resiliency and strength, this including the ability to stretch and dependably return to an initial length.

In each of the embodiments subsequently described, the plastics incorporated both into the joint defining end bone faces, as well as the outer urethane or other deformable coverings associated with the artificial ligaments, are constructed of a sanitized or sterilized material and which may further include an integrally incorporated antibiotic compound. The internal filament portions associated with each ligament design may further include such as graphite, other synthetic fibers including high strength polyester/nylon, as well as natural/cellulose based materials, including in particular very fine bamboo threads and which have been found to be extremely durable.

End locations of the ligaments include larger bead-like portions, see at 28 and 30, these being connected to ends of the central fiber/filament 26. Upon translating a central projecting location of the filament 26 (see at 32 in FIG. 3), this in turn causes the bead portions 28 and 30 to inwardly displace and outwardly deform end defined pockets, further at 34 and 36, associated with the urethane covering.

Figure 2:
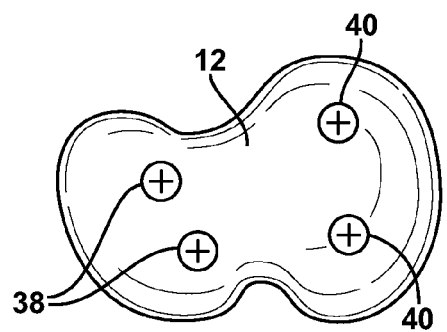
FIG. 2 is an end view illustration of a selected artificial implant bone according to FIG. 1 and showing the manner in which bore holes are drilled at precise locations for receiving inserting ends of associated ligament supports.
Figure 2A:
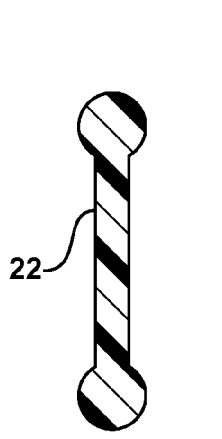
FIG. 2A is a partial illustration of a selected ligament, such as shown in FIG. 2.

FIG. 2 is an end view illustration of a selected artificial implant bone, such as again at 12 in FIG. 1 and which illustrates a plurality of bore holes, see pairs 38 and 40, drilled at precise locations for receiving inserting ends of associated ligament supports, e.g. the bead portions 28 and 30. A particularly configured tool, such as incorporating an expandable and spherical grinding tip, is employed for grinding the desired configuration of hole into the end or proximate side facing locations of both opposing bones, this in particular contemplating forming a larger diameter interior location communicated through a narrowed surface communicating channel. Upon snap-fit inserting of the urethane end pockets and each associated bead portion, subsequent expansion in the manner previously described causes the end location of the ligament to be securely anchored into the drill hole.

Figure 2B:
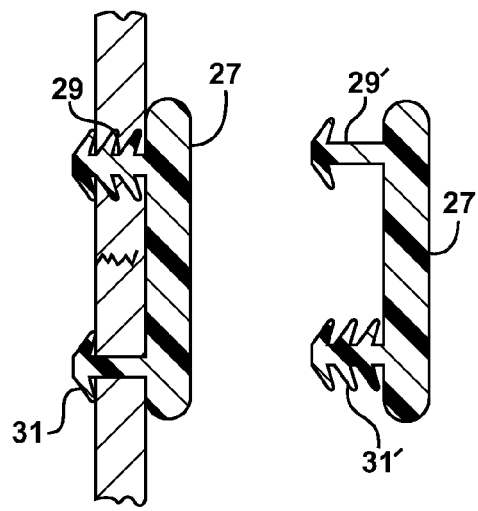
FIG. 2B is an illustration of an alternately configured and press fit ligament structure, this possessing an elongated body with laterally projecting and barbed side sections which are "press fit" into engagement with side disposed locations of a selected bone or pair of bones located in closely proximate fashion.

FIG. 2B is an illustration of an alternately configured and press fit ligament structure, at 27, this possessing an elongated body with laterally projecting and barbed side sections, at 29 and 31, and which are "press fit" into engagement with side disposed locations of a selected bone or pair of bones located in closely proximate fashion. The ligament structure illustrated in this embodiment is intended for certain applications, such as where there is a hairline crack or other imperfection in an existing bone/implant application and it is desired to repair or remediate the damaged area without requiring removal from the patient. As also shown, the spaced apart and barbed extending side edges can be alternately configured, see at 29' and 31', in order to establish a desired snap-fit engagement with a selected bone drill aperture. This can also entail a plurality of deflecting ridge/gripping portions or the provision of end deflectable and biasing locations for anchoring in place once passed through the depth of the bone wall.

Referencing again FIG. 3, a first illustration of the ligament sub-assembly illustrates the expandable urethane end pockets in a pre-tensioned, pre-anchored condition. As described, and once opposite ends of the ligament are located through the mounting drill hole locations associated with first and second opposing and joint defining bones, the tensioning of the central filament portion 32 of the synthetic fiber strands, results in the expansion of the pockets (see FIG. 3A). Referencing further FIG. 3B, a succeeding illustration to that shown in FIG. 3 references the fibrous/thread 26 being progressively displaced (and by drawing inwardly the bead end portions 28 and 30 against the curvature of the urethane end pockets 34 and 36, in order to outwardly deform the outer urethane material associated with the ligament ends in biasing fashion against the arcuate inner walls of the bone drill hole.

Referring now to FIG. 4, an illustration is shown of a ligament structure according to another embodiment and illustrating a plurality of ring-shaped ligaments 38, 40, 42, et. seq., securing first 44 and second bones 46 according to a further preferred application. The bones 44 and 46 each include lubricated plastic defined end surfaces, at 48 and 50, these defining an intermediate joint region.

The ligament structure of the rings 38, 40, 42, et. seq., is similar to that previously described, and such as again including an outer and deformable urethane material, within which is encased an inner translating filament. Accordingly, and in one mounting variant, the ligaments are arcuate (semi-circular at most), with opposite expandable ends 52 and 54 seating in dedicated bone drill hole locations, these also being shown in the end view of FIG. 5 at 56 and 58 as sets of holes.

Of note, and further referencing FIGS. 6-6B, the ligaments can exhibiting modified expanded ends that can also be reconfigured, such as is shown in FIG. 6B, such that they can be made to seat together (such as by being configured as male and female engaging portions), and in order to convert an arcuate shape ring with first and second bone anchoring ends as a dedicated circular or ring shaped ligament. FIG. 6B illustrates a modified version of the circular shaped ligament shown in FIG. 6A, and by which a snap fit engagement, see male end at 60 and associated outer female end 62 is established for securing the artificial ligament in engaged fashion.

Referring now to FIG. 7, an illustration is shown of an alternate mounting variant for securing a reconfigured artificial ligament 64 to first 66 and second 68 locations associated with a unique joint defining structure. Artificial bones are illustrated at 70 and 72 and generally correspond to an alternate joint defined structure, such as possibly an elbow structure and in which bone hole locations 66 and 68 again correspond to drilled locations through which bead end portions 74 and 76 and corresponding urethane end pockets 78 and 80 are resistance inserted, and subsequently deformed in the manner previously described, and such as through the translation of dedicated end defined fiber threads of intermediate length, at 82 and 84. The central extending portion of the ligament body 64 as such does not exhibit the fiber threads, however the construction of the ligament body is such that it can withstand the normal forces associated with the joint application in both a dynamic and resilient fashion.

Figure 8:
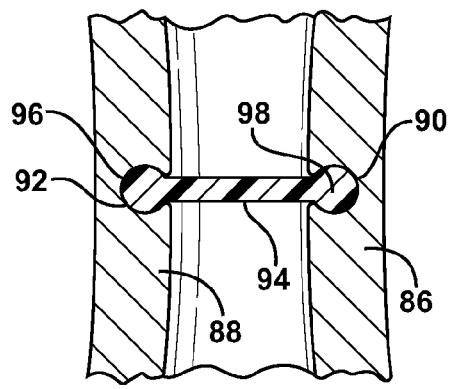
FIG. 8 is a sectional illustration of a further mounting configuration for application to opposing inside walls of a selected bone according to the present inventions.

Referring now to FIG. 8, a sectional illustration of a further mounting configuration of a ligament associated with inside opposing surfaces of a selected bone. In particular, the bone (again typically artificial but also contemplating possible application to actual bones) illustrated in cutaway includes wall portions 86 and 88. Drill holes, of a nature previously described, are effected at 90 and 92 associated with inside facing locations of the bone wall portions 86 and 88 and utilizing any specialized medical drills and techniques which render possible this drill configuration. The ligament is illustrated at 94 and includes opposite and expandable ends 96 and 98 which, upon being engaged in a fashion similar to that previously described, serves to assist or reinforce in maintaining the internal integrity of the bone structure.

Figure 9:
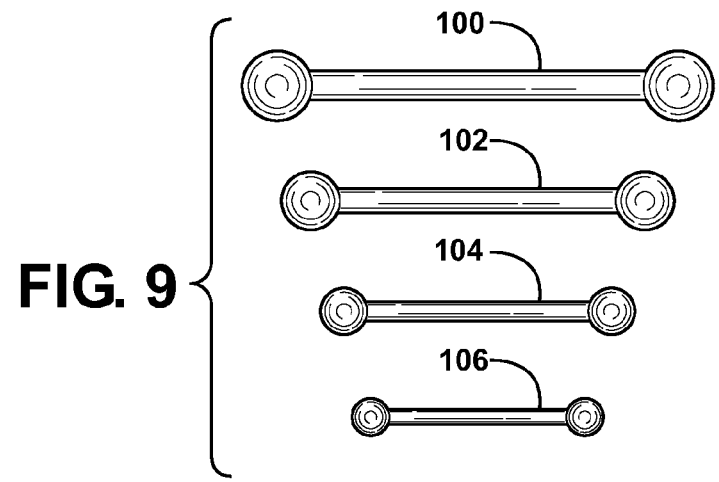
FIG. 9 is an illustration of a plurality of individual configured artificial ligaments according to the present inventions.

FIG. 9 is an illustration of a plurality of individual configured artificial ligaments, see at 100, 102, 104 and 106, according to the present inventions. In particular, each of the ligaments referenced corresponds to a differently sized application for engagement into specifically configured bone drill holes, such as for example in the manner previously described.

Figure 10:
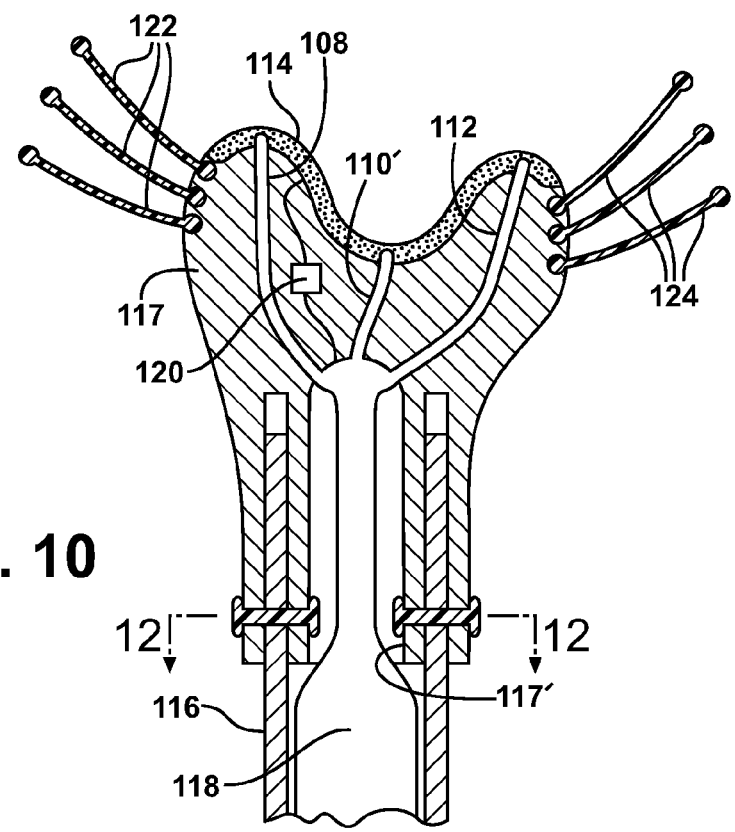
FIG. 10 is a cutaway illustration of a further example of a ligament supported implant and joint, and further showing a plurality of conduit passageways formed into an end surface of a selected artificial bone containing a synthetic fluid reservoir, and which is micro-controlled for discrete release of lubricant fluid s into the joint.

Referring now to FIG. 10, a cutaway illustration of a further example of a ligament supported implant includes a plurality of conduit passageways 108, 110, 112, these being formed into an end surface 114 of a selected artificial bone 116. As will be further described in reference to FIGS. 12 and 13A-13C, an implant section 117 is anchored to an end of the bone 116, such as through the use of a plurality of anchoring portions.

The passageways communicate with a surface of the end secured implant section 117, in turn anchored to the bone 116 such as by bolts or fasteners. A synthetic fluid reservoir 118 is contained within a hollow interior of the bone 116 and is micro-controlled (see controller representatively shown at 120 with sensors) for instructing discrete release of lubricant fluid s into the surface location 114 defining a part of the joint area. The surface 114 may further again include a low resistance and antiseptic plastic/wear layer, this being continually augmented by the microcontroller dispensed droplets (such as for example constituting a ½ drop release on a daily basis. Additional features such as ligaments are representatively shown at 122 and 124, and such as can be constructed in a fashion similar to that previously described.

Figure 11:
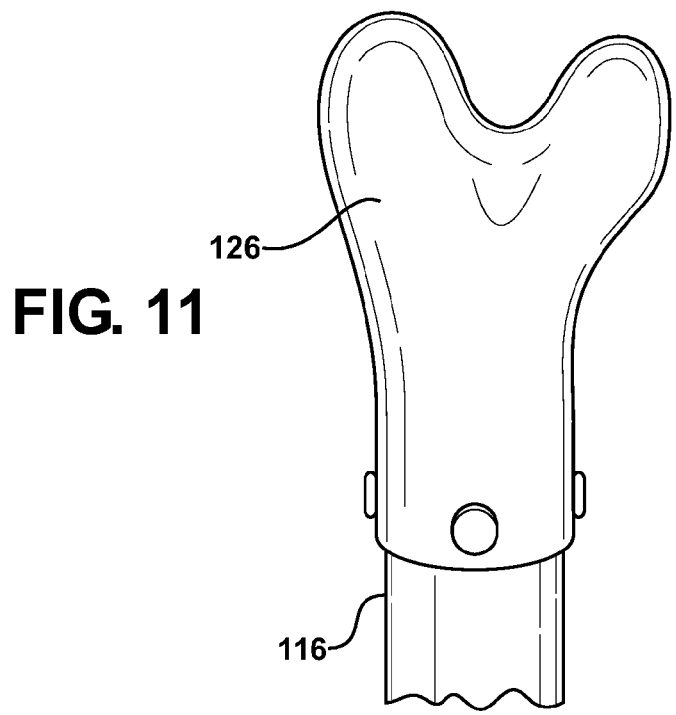
FIG. 11 is an illustration of a further variant similar to that shown in FIG. 10, and of a ligament supported joint configuration.

Referring now to FIG. 11, an illustration is shown of a further variant, similar to that shown in FIG. 10, and of a ligament supported joint configuration. In particular, an alternately configured end implant section 126 is shown anchored to an end of a suitable and artificial bone, again at 116. The implant section 126 can correspond to any of a number of suitable joint defining sections, and such as can be arranged in opposing fashion with the arrangement shown in FIG. 10.

Figure 12:
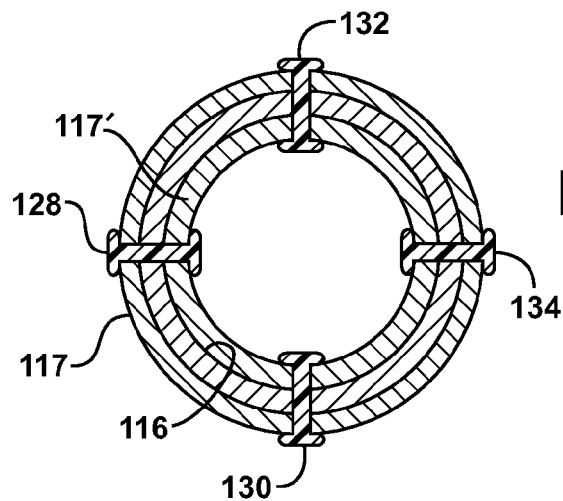
FIG. 12 is a cutaway view taken along line 12-12 of FIG. 10 and illustrating a plurality of plasticized plugs for coaxially securing an end-defined implant section over an elongate, open ended and interiorly hollowed artificial bone.

FIG. 12 further shows a cutaway view, taken along line 12-12 of FIG. 10, and illustrating a plurality of plasticized plugs or anchors, see at 128, 130, 132 and 134, for coaxially securing an end-defined implant section, again at 117, over an elongate, open ended and interiorly hollowed artificial bone 116. When viewed collectively, FIGS. 10 and 12 illustrate the annular defined space associated with the seating end of the implant section 117 (see also spaced apart inner wall 117'), the annular edge of the bone 116 seating in the space between the implant end walls 117 and 117', with the bolt or fastener sections 128-134 being secured at the locations indicated.

Figures 13A, 13B, 13C:
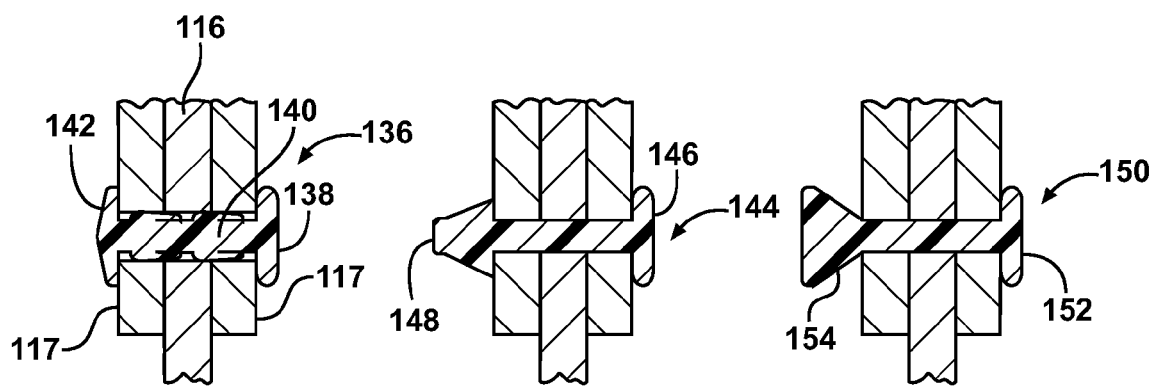
FIG. 13A is an illustration of a first configuration of a plasticized anchor and such as is shown in the embodiment of FIG. 12.
FIG. 13B is an illustration of an alternately configured anchor.
FIG. 13C is a still further illustration of another synthetic anchor.

Referring now to FIG. 13A, an illustration of a first configuration of an alternately configured plasticized anchor, such as is shown in the embodiment of FIGS. 10 and 12, is referenced at 136. The anchor 136 includes a flattened outer end 138 from which extends an elongated stem portion 140, this further including a plurality of spaced apart tangs 142 and which extend in a fashion which biasingly engage the inner annular wall surfaces of the inner and outer spaced apart implant walls (see again at 117 and 117') as well as the seatingly fitted annular bone 116 disposed therebetween.

As further shown in FIG. 13B, an alternately configured anchor 144 includes a similarly flattened end 146 and an enlarged tip 148 for resistively engaging against an inside surface of the implant wall 117'. FIG. 13C is a still further illustration of another synthetic anchor, see at 150, and which includes a likewise flattened first seating head 152, and opposite extending and conically flared end 154 again corresponding to an inner wall seating location for securing the implant 117 to the associated bone 116.

FIG. 14 is an illustration similar to that shown in FIG. 10 of a yet further anchor bolt design utilized in the securing of an end defined implant section, at 156, over a bone 158, such as similar to that previously shown in FIG. 12. The anchor bolt is further shown at 160 and is likewise constructed of a synthetic plastic, including opposite end positioned enlarged heads 162 and 164, which secure the spaced apart and annular extending rim locations 166 and 168 of the implant 156 to the open annular edges of the bone 158. Of further note, the implant 156 can be constructed of a molded plastic or other synthetic material, and may again include a lubricated joint defining surface 170, as well as pluralities of ligaments 172 and 174 which, in cooperation with a further suitable bone, define a desired joint application.

Referring next to FIG. 15, an alternate embodiment is referenced for securing an end section implant, at 176, over an open interior and elongate artificial bone 178. This in particular involves the ability to undercut (e.g. machine/drill) sections established in the outer annular bone surface, see at 180 and 182. These undercut sections are configured to inter-fit with a corresponding and annular interior configuration, see inwardly facing annular protrusions 184 and 186, associated with a depending skirt portion 188 of the annular end implant section 176. A central plug location 190 of the implant is dimensioned such that it extends into the interior of the bone 178 and, in cooperation with the mating undercut and annular projecting locations, ensure a secure fit of the end-implant section 176 over the end of the bone 178.

Referring to FIG. 16, a non-cutaway illustration is shown of the embodiment of FIG. 15, this further illustrating the feature of the plastic bands, see at 192 and 194, for assisting in securing the end-fitted implant section 176 over the hollow bone 178. The bands can either be surface located, as indicated in FIG. 16 or, alternatively, can be in-molded into the interior of the implant's annular skirt portion 188, as shown in FIG. 15 at 192' and 194'.

Referring now to FIG. 17, an exploded view is shown of a connective artificial ligament, see at 200 incorporated into a joint defined (e.g. such as knee or elbow) implant according to one embodiment of the present invention. The arrangement of FIG. 17 includes a first bone 202 defined ball projection 204 and an associated second bone 206 with an interiorly defined socket 208 for establishing, in combination with the connective ligament 200 extending therebetween, effortless contact between opposing bone end surfaces.

As further understood, the bones 202 and 206 are typically artificial prostheses, these including such as plastic, metal or other suitable material constructions which exhibit the necessary properties of durability and resilience. Opposing and mating lubricating plastic surfaces (or rings), see at 210 and 212, are provided in such as ring-shaped components secured to the respective bones 202 and 206, such as in the case of lubricating surface (or ring) 210 around a neck portion 214 associated with the ball projection 204 and in the further case of the coacting lubricating ring 212 being secured to an encircling rim location of the bone 206 located around the interiorly defined socket 208. Upon assembly, the rings 210 and 212 contact one another in a mating and relatively rotational permissive fashion, and in order to promote effortless contact between opposing bone end surfaces.

As will be further described with reference to each of the succeeding illustrations the ligaments (again shown at 200 in FIG. 17) are each typically constructed of a fibrous based central core over which is molded an expandable urethane or other suitable material, and such that the ligament exhibits the concurrent properties of significant durability, resiliency and strength, this including the ability to stretch and dependably return to an initial length.

In each of the embodiments subsequently described, the plastics incorporated both into the joint defining end bone faces, as well as the outer urethane or other deformable coverings associated with the artificial ligaments, are constructed of a sanitized or sterilized material and which may further include an integrally incorporated antibiotic compound. The internal filament portions associated with each ligament design may further include such as graphite, other synthetic fibers including high strength polyester/nylon, as well as natural/cellulose based materials, including in particular very fine bamboo threads and which have been found to be extremely durable.

In the embodiment of FIG. 17, the ligament 200 (illustrated in partial cutaway) extends between a first connective location 216 associated with the ball projection 14 of the bone 202 and a second connective location 218 associated with the interiorly defined socket 208 of the second bone 206.

FIG. 18 is an exploded plan view illustrating a further variant of ligament assembly and in which a lubricated plastic layer 220 surrounds a ball-end defined projection 222 of a first bone and further exhibits an integrally formed, bulbous male end projecting ligament seating portion 224, extending via an interconnecting neck 226. The bulbous end seating portion 224 is resistively snap-fit received into an associated located recess 228 defined in a female and additional bone defined socket cavity 230, for flexibly and dynamically retaining the first bone ball portion within the second bone socket of a selected artificial implant bone.

The associated bore hole, see again at 228 in FIG. 18, is drilled at a precise location within the second bone receiving socket, such as through the use of a particularly configured tool, such as incorporating an expandable and spherical grinding tip, and which is employed for grinding the desired configuration of hole into the end or proximate side facing locations of both opposing bones. This in particular contemplates forming a larger diameter interior location communicated through a narrowed surface communicating channel, see at 232. Upon resistive snap-fit of the bulbous end portion 224 of the ligament secured to the such as the first bone lubricating layer 220, through the employment of a suitable tool and concurrent with attaching the ball 222 into the socket 230, the ligament is securely anchored into the drill hole.

FIG. 19 is an exploded plan view of a further configuration of ligament assembly, similar to that shown in FIG. 18, and by which the arrangement of lubricating plastic layer 234 and associated bulbous end ligament projection 236 is switched to a female bone and ball defined socket 238. A corresponding male ball projection 240 incorporates an interior defined drill recess 242 (similar to that previously described with reference to elements 228 and 232 in FIG. 18) and for resistively seating the ligament projection.

Figure 20A:
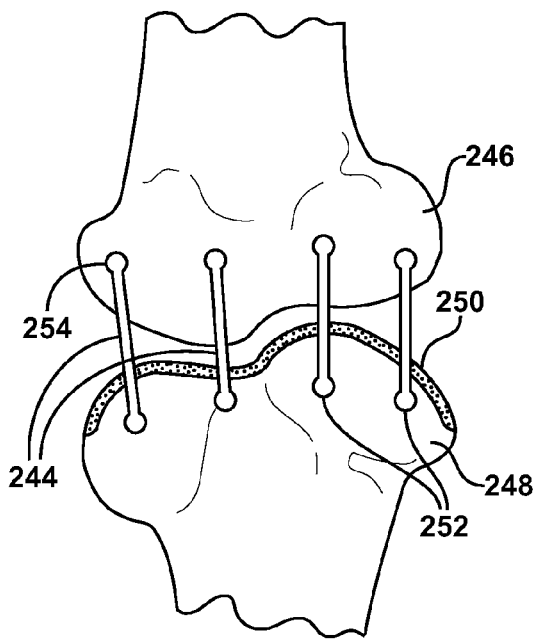
FIG. 20A is an illustration of a plurality of individual and smaller sized ligaments extending between seating locations associated with opposing and joint defining bones, a lubricated plastic layer being established between the bones and, in combination with the ligaments, providing a joint such as between tibia and fibula design bones.

Referring now to FIG. 20A, an illustration of a plurality of individual and smaller sized ligaments is referenced at 244 extending between seating locations associated with opposing and joint defining bones 246 and 248. A lubricated plastic layer 250 is established between the bones 246 and 248 and, in combination with the ligaments 244, provide a joint such as between tibia and fibula design bones.

Figure 20B:
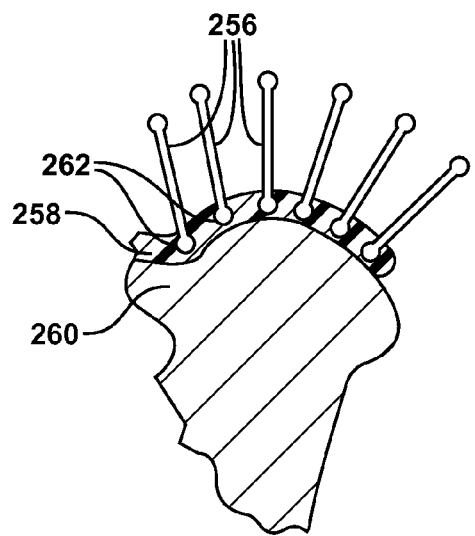
FIG. 20B is an enlarged sectional illustration of an alternate ligament assembly and which a plurality of ligament ends are formed within a sanitary plasticized layer in turn defined upon a selected end surface of a bone.

The ligaments 244 are further secured in recessed fashion within the bones, as shown in at 252 and 254 for bones 246 and 248, respectively, in FIG. 20. This can be accomplished such as by pre-forming or pre-manufacturing the ligament ends into the end-facing bone structure. Alternatively, and further referencing FIG. 20B is an enlarged sectional illustration of an alternate ligament assembly shows a plurality of ligament ends 256 which are formed within a sanitary plasticized layer 258 in turn defined upon a selected end surface of a bone 260. As in FIG. 20A, enlarged end seating locations 262 are referenced within the plasticized layer 258 and provide for fixed engagement of the ligaments in dynamic fashion.

Figure 21:
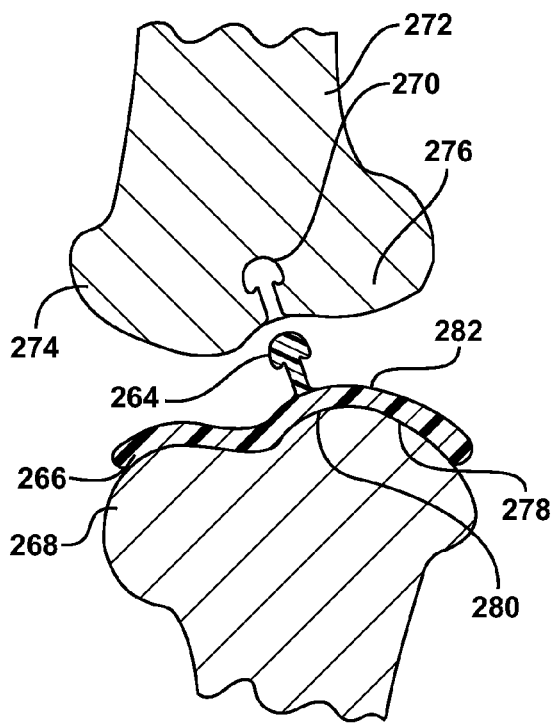
FIG. 21 is an illustration of a knee joint assembly and illustrating a ligament engaging portion extending from a plasticized layer associated with a first lower leg bone and seating within an interiorly drilled and resistively seating aperture associated with an upper femur bone.

FIG. 21 is an illustration of a knee joint assembly including a ligament engaging portion 264 extending from a plasticized layer 266 associated with a first lower leg bone 268, and seating within an interiorly drilled and resistively seating aperture 270 associated with an upper femur bone 272. The plasticized layer 266 is similar to those previously described in reference to earlier embodiments and can define a softer plastic cartilage with a substantially frictionless and supporting surface, against which co-act associated projecting end locations 274 and 276.

In a preferred embodiment, the plasticized layer 266 is supported in loosely supported fashion of its associated underside contoured surface 278 relative to an opposing surface 280 of the lower bone 268. In this manner, the anchoring of the integrally defined ligament portion 264 extending from an associated upper contoured surface 282 of the plasticized layer 266, and within the upper bone 272, establishes a desired and substantially frictionless dynamic environment for a completed joint assembly.

Figure 22:
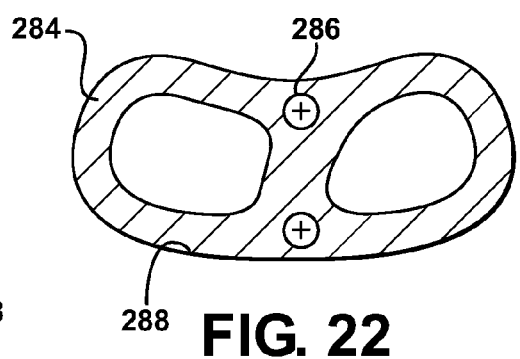
FIG. 22 is a cutaway end view of a tibia bone, such as shown in FIG. 4, and illustrating an alternative arrangement of ligaments according to the present inventions.

Referring to FIG. 22, a cutaway end view is shown of a tibia bone 284, such as shown in FIG. 20, and which further illustrates an alternative arrangement of ligament structure, see at 286 and 288. The cutaway ligaments 286 and 288 can define such as a loop shape or other seating arrangement for securing the associated bone 284 to an opposing bone not shown) in a desired and ligament defining dynamic environment.

Figure 23:
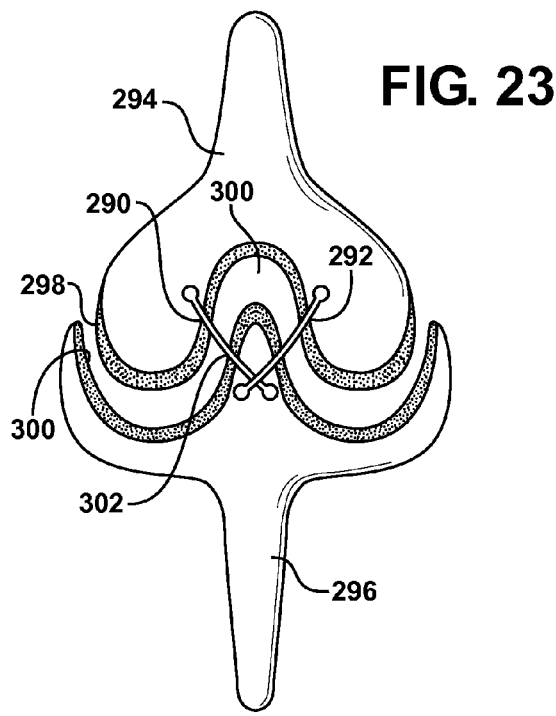
FIG. 23 is plan view of a further joint assembly and including a pair of crosswise extending ligaments secured to opposing and joint defining surfaces associated with first and second artificial end plugs, and such as which can be secured in retrofit manner to natural bones.

Referring now to FIG. 23, a plan view is shown of a further joint assembly and including a pair of crosswise extending ligaments, at 290 and 292, secured to opposing and joint defining surfaces associated with first and second artificial end plugs 294 and 296. As will be further described in succeeding illustrations, the end plugs 294 and 296 are constructed of a hardened plastic, or composite, material, and exhibit lubricious inducing cartilage end surfaces, at 298 and 300 respectively, and such as which can be secured in retrofit manner to natural bones.

Figure 24:
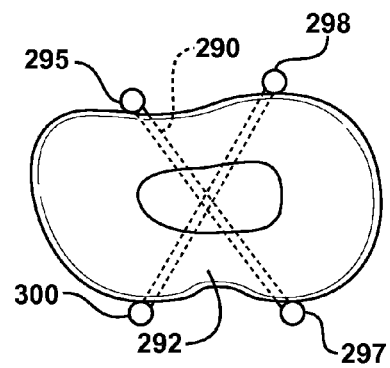
FIG. 24 is a modified end plan view illustrating connecting locations of the pair of ligaments relative to opposing bone end surfaces.

As will also be described in additional detail, the end plugs 294 and 296, as well as those shown in succeeding embodiments, are generally illustrated in a cutaway cross section and it is understood and envisioned that a three dimensional representation of the joint defining bone locations (while not practicable for purposes of the present description) can also contemplate a 360 degree socket receiving cavity (see as shown at 300) associated with the first end plug 294 receiving in generally inserting fashion a male projecting end (at 302) associated with the second end plug 296. As is also shown in the modified end plan view of FIG. 24, better illustrated are the connecting locations associated with the pair of ligaments 290 and 292 secured relative to opposing bone end surfaces.

Specifically, enlarged (bead) ends are associated with the ligaments, as referenced at 295 & 297 for ligament 290 and at 298 & 300 for ligament 292. The ligaments 290 and 292 are constructed in one non-limiting variant off an elongated fiber/graphite composite material, with the enlarged bead shaped ends further being secured within recess cavities, these created by specialized bone drill forming bits at locations proximate side or end surface interior locations formed in the end plugs 294 and 296. The recess formed cavities also can include an enlarged diameter recess interior interconnected to the surface of the bone end plug via a narrower diameter neck.

It is also envisioned that, in addition to drilling the desired cavities, unique and innovative forming techniques can be employed for producing the desired ligament engaging locations as part of the plasticized end plug. Although not clearly shown in this illustration, it is also understood that the bead ends can each also exhibit an end-directed plasticized displaceable component for securably maintaining the bead ends within their associated recessed cavities, and once press-fit inserted within the recess drill cavities.

Figure 25:
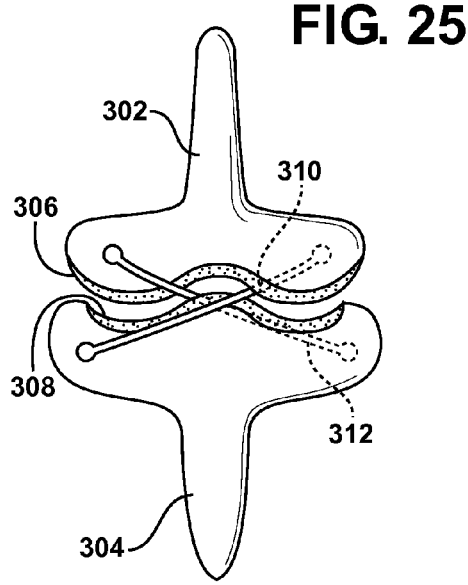
FIG. 25 is a similar illustration to that of FIG. 7 and showing an alternate arrangement of bone and joint with stretchable composite ligaments.

Referencing FIG. 25, a similar illustration to that of FIG. 23 shows an alternate arrangement of bone, see end plugs 302 and 304 with opposing and lubricant defining (soft plastic) cartilage defining surfaces, at 306 and 308, and joint with stretchable composite ligaments 310 and 312. As disclosed in the preceding embodiment, the ligaments can be arrayed in a crosswise extending pattern and to thereby provide both a combined degree of stretch/elastic give to the defined joint, as well as maintaining the overall integrity of the joint assembly over prolonged dynamic use.

Figure 26:
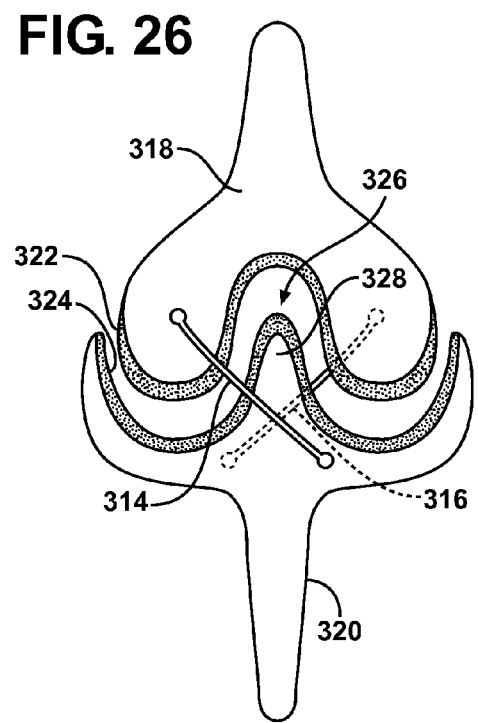
FIG. 26 is a further cutaway view of a slightly alternately configured joint assembly with recess mounted ligaments.

FIG. 26 is a further cutaway view of a slightly alternately configured joint assembly with recess mounted ligaments, see at 314 and 316, and which are secured in extending and cross wise fashion between a modified pair of end plugs 318 and 320. A series of mating peaks and ridges established between the end opposing faces, these also including lubricant cartilage layers 322 and 324, associated with a soft plastic material overlaying hardened plastic substrates establishing the end plugs 318 and 320. The first end plug 318 further establishes a more pronounced interior (central) cavity 326, within which seats a generally central and inner projecting portion 328 associated with the second plug 320. As explained previously, the end plugs are shown in sectional cutaway, it being understood that they each define a substantially three dimensional article, with the inner portion 328 and opposing cavity 326 establishing a universal and joint defining pocket therebetween.

Figure 27:
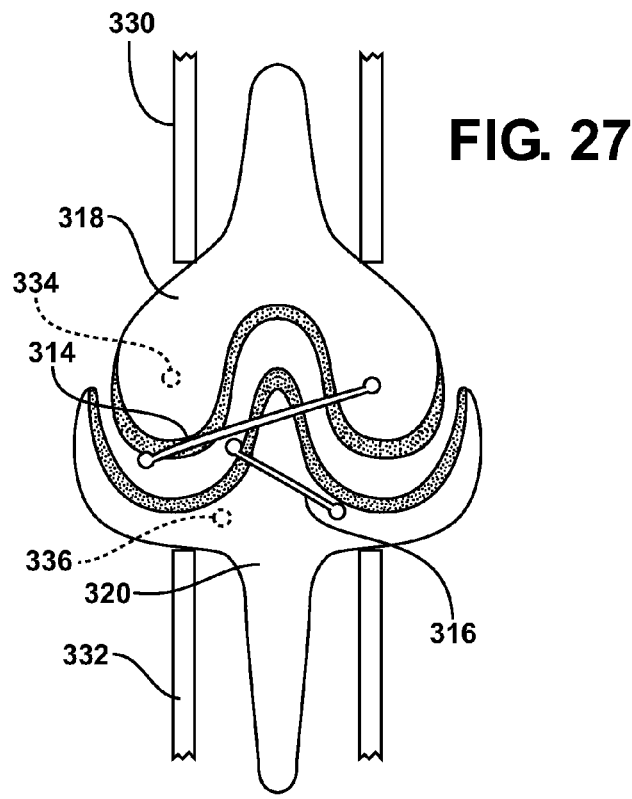
FIG. 27 is an illustration similar to that shown in FIG. 10 and illustrating the manner in which the bone end plugs are secured to the retrofit machined bones and subsequently attached by a pair of cross extending (interlocking) stretch and secure ligaments.

As also previously described, enlarged bead-ends of the ligaments 314 and 316 are installed in a similar previously described fashion, and such as in which a pre-formed and enlarged inner diameter hole receives the associated bend end in a press fit fashion, following which a deformable plastic may be optionally inserted, injected or linearly compressed along end extending locations associated with the ligament strand, and to thereby retain the bead in securely in place. As further shown in FIG. 27, illustrated is the manner in which the bone end plugs 318 and 320 are secured to retrofit end machined bones (e.g. these being natural bones and which are shown at 330 and 332 with sectioned off ends).

The hardened plastic end plugs 318 and 320 are fixedly secured to the sectioned ends of the bones 330 and 332. Following this, the ligaments 314 and 316, which are already secured at first selected bead ends, are manipulated such that the opposite bead ends are resistively press fit into engagement with pre-formed recess cavity defined apertures, see as shown at 334 and 336, such that the joint assembly exhibits a pair of cross extending (interlocking) stretch and secure ligaments.

Figure 28:
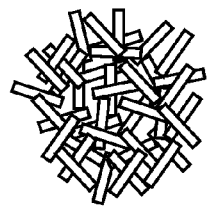
FIG. 28 is a prior art illustration of a section of healthy regenerating bone.
Figure 29:
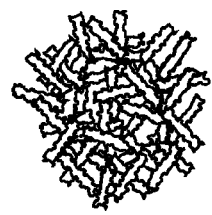
FIG. 29 is a prior art illustration of a section of deteriorating bone.
Figure 30:
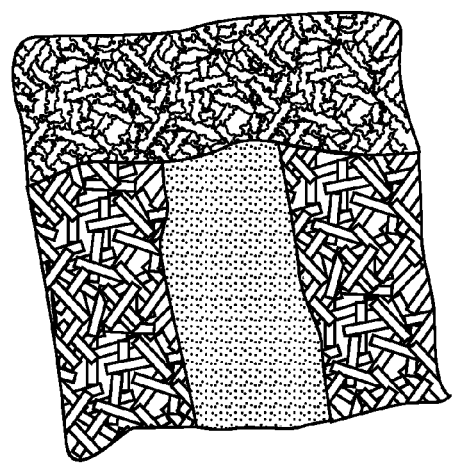
FIG. 30 is a further prior art illustration of a portion of deteriorating bone residing atop an underlying and rejuvenating bone layer and associated inner bone marrow.

Referring now to FIGS. 28-30, a succession of illustrations are shown of known bone structures, and such as are relevant to the incorporating of the joint plugs. Specifically, FIG. 28 provides a microscopic illustration of healthy bone growth associated with healthy bone marrow and such as which can assist in permanently affixing the plug inserting ends of the joint defining hardened plastic components, see again as shown in FIG. 27 at 318 and 320 and which are inserted within the sectioned natural bone ends 330 and 332, further within which human bone marrow resides for facilitating the desired natural bonding of the plug to the bone. FIG. 29 in contrast is a prior art illustration of a section of deteriorating bone, whereas FIG. 30 is a further prior art illustration of a portion of deteriorating bone residing atop an underlying and rejuvenating bone layer and associated inner bone marrow.

Figure 31:
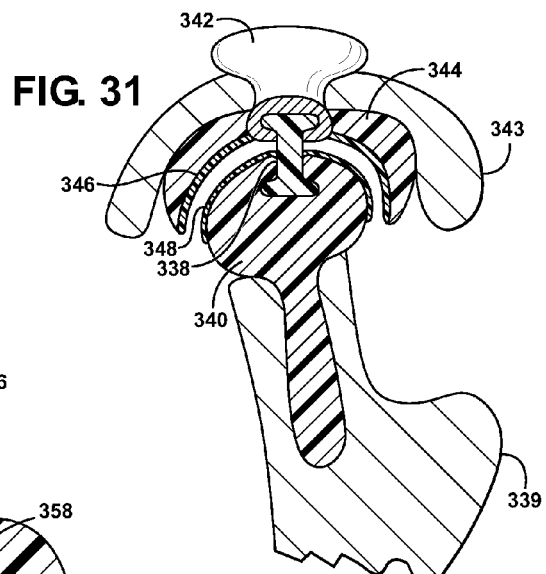
FIG. 31 is an illustration of a further variant of swivelable joint assembly and in which a rotating flexible ligament of substantial spool shape is arranged in a socket configuration between a lower male end defining bone and an undercut support secured to an upper socket defining bone.

Referring now to FIG. 31, an illustration is shown of a further variant of swivelable joint assembly and in which a rotating flexible ligament of substantial spool shape 338 is arranged in a socket configuration between a lower male (or receiver) end defining bone 339, including composite hard plastic end plug 340 and an undercut support 342 secured to an upper socket defining bone 343 further including a likewise hard plastic arranged in a generally bowl-receiving shape 344. The arrangement shown in FIG. 31 can depict such as a hip or shoulder joint, and in which a desired degree of combined universal and rotatable support is established by the artificially constructed joint. As shown in previously described embodiments, opposing surface locations associated with the composite hard plastic bones 340 and 344 further include composite soft plastic surfaces 346 and 348, the first hardened plastic plug 340 further including an extending stem portion which is securably mounted within an interior associated with the bone 339, whereas the second bowl shaped hardened plastic is secured via adhesives or a naturally ribbed or irregularly shaped surface for promoting natural bone marrow incorporation and adhesion to the upper bone defined socket 343.

The undercut support 342 is further provided in a generally knob-shape or configuration, and which can also be constructed of a suitable durable plastic or like composite material, and which is secured within an aperture formed through the upper saucer shaped bone 343 and associated hardened plastic 344. The rotating flexible (e.g. spool shaped) ligament 338 is swivelable both in respect to the upper located undercut support 342, as well as the recessed (e.g. press fit) mounting location associated with the lower male defining plug 340. In a preferred application, the knob shaped undercut support can also rotate independently or in unison with the spool shaped ligament 338.

Figure 32:
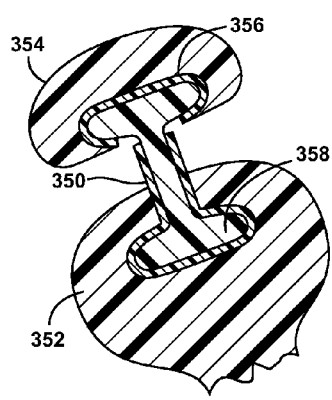
FIG. 32 is an enlarged sectional view of a modified spool shaped rotating and flexible ligament disposed between swivelable contact locations associated with receiver/socket composite hardened plastic end plugs.

Progressing to FIG. 32, an enlarged sectional view is shown of a further variant of spool shaped rotating and flexible ligament, at 350, disposed between swivelable contact locations associated with a modified and composite hardened plastic lower installed end plug 352 and an upper hardened plastic end plug 354. The spool shaped ligament 350 differs from that previously identified at 338 in that a first exterior layer 356 is applied over a second core material 358. In one preferred application, the exterior layer 356 is a softer/cushioning material, as compared to a hardened core 358. It is also understood that the material compositions can be reversed with the core incorporating a softer material and in comparison to a hardened outer layer, this providing variances in the performance characteristics of the universal joint in use.

Figure 33:
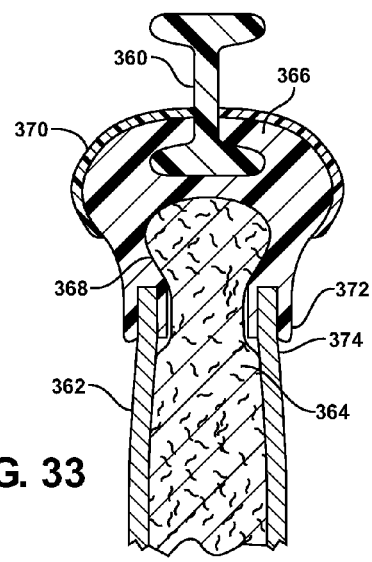
FIG. 33 is an illustration of an alternate arrangement to that shown in FIGS. 15 and 16, and by which a differently configured hardened plastic end plug is secured to a sectioned end of a natural bone, within which is contained bone marrow, the end plug further exhibiting a recessed interior facing surface which is ribbed or otherwise irregularly formed so that marrow contact locations promote the growth of adhering healthy bone.

Finally, and referring to FIG. 33, an illustration is shown of an alternate arrangement to that shown in FIG. 31 or 32, and by which a differently configured hardened plastic end plug, likewise generally spool shaped as shown at 360, is secured to a sectioned end of a natural bone 362, within which is contained bone marrow 364. An associated end plug 366 further exhibits a recessed interior facing surface 368 which is ribbed or otherwise irregularly formed, and such that marrow contact locations promote the growth of adhering healthy bone. The plug 360 is further illustrated in a recess cavity secured (or press fit) fashion within an exposed end face location of the hardened plastic plug 366, and over which is applied a softer plastic cartilage defined surface 370. As is further shown in FIG. 33, an annular end face of the plug 366 can exhibit an interior notched recess 372, this being configured and dimensioned to seatingly engage over the exposed and sectioned end (see at 374) of the retrofitted bone 362, at which point the interiorly contained marrow 364 initiates its natural bonding action between the hardened plastic plug 366 and the bone 362.

Having described my invention, other and additional preferred embodiments will become apparent to those skilled in the art to which it pertains, without deviating from the scope of the appended claims.

I claim:

1. A ligament adapted for use in a joint established between first and second bones, said ligament comprising:
    an elongated body constructed of a plasticized material and terminating at opposite ends in deformable pockets;
    a filament extending within said elongated body and connecting at said opposite ends in to enlarged beads seated within said deformable pockets;
    said filament including an intermediate projecting portion extending through said body and connecting to said beads; and
    said beads and associated pockets adapted to being resistively anchored within undercut profiles formed into joint defining surfaces of each bone such that, outwardly displacing said central projecting portion of said filament causes said beads to inwardly displace against said pockets so as to deform said pockets around said beads and within the undercut profiles, said ligament establishes a dynamic and resilient connection between the bones.

2. The invention as described in claim 1, said ligament further comprising an outer urethane body.

3. The invention as described in claim 1, said filament further comprising at least one of a graphite, a nylon, a polyester, and a cellulosic fiber strand material.

4. The invention as described in claim 1, said plasticized material having a specified shape and size and further comprising an antimicrobial plastic.

* * * * *